United States Patent
Shen

(10) Patent No.: US 9,133,955 B2
(45) Date of Patent: Sep. 15, 2015

(54) FLOW CONTROL PROPORTIONAL VALVE

(71) Applicant: Beijing Aeonmed Co., Ltd., Beijing (CN)

(72) Inventor: Youfang Shen, Beijing (CN)

(73) Assignee: Beijing Aeonmed Co., Ltd., Beijing (CN)

(*) Notice: Subject to any disclaimer, the term of this patent is extended or adjusted under 35 U.S.C. 154(b) by 49 days.

(21) Appl. No.: 14/002,659

(22) PCT Filed: Dec. 25, 2012

(86) PCT No.: PCT/CN2012/087404
§ 371 (c)(1),
(2) Date: Oct. 11, 2013

(87) PCT Pub. No.: WO2013/097700
PCT Pub. Date: Jul. 4, 2013

(65) Prior Publication Data
US 2014/0054479 A1    Feb. 27, 2014

(30) Foreign Application Priority Data
Dec. 30, 2011   (CN) .......................... 2011 1 0458116

(51) Int. Cl.
*F16K 31/06* (2006.01)
*A61M 39/22* (2006.01)
(Continued)

(52) U.S. Cl.
CPC ............ *F16K 31/0655* (2013.01); *A61M 16/20* (2013.01); *A61M 16/203* (2013.01); *A61M 39/22* (2013.01); *F16K 31/082* (2013.01); *G05D 7/0635* (2013.01); *Y10T 137/7761* (2015.04)

(58) Field of Classification Search
CPC ............ F16K 31/0655; F16K 31/0672; F16K 31/082; A61M 16/203; A61M 16/204; A61M 16/205
USPC .................................. 251/14, 129.08, 129.17
See application file for complete search history.

(56) References Cited

U.S. PATENT DOCUMENTS 5,771,884 A     6/1998  Yarnall et al.
5,927,275 A *   7/1999  Loser et al. ............. 128/205.24
(Continued)

FOREIGN PATENT DOCUMENTS

CN     201133471 Y    10/2008
CN     201149125 Y    11/2008
(Continued)

OTHER PUBLICATIONS

International Search Report issued in International Application No. PCT/CN2012/087404 dated Mar. 21, 2013.

*Primary Examiner* — Matthew W Jellett
(74) *Attorney, Agent, or Firm* — Venable LLP; Robert Kinberg

(57) ABSTRACT

A flow control proportional valve comprises a valve body and a valve core disposed below the valve body, a valve cover plate is disposed at an upper end of the valve core, the bottom of the valve cover plate is connected to an upper end of a connection rod, a coil rack fixedly mounted at a lower end of the connection rod is wound by an enameled wire which is connected to a power supply unit, a magnetic core and a magnetic ring are disposed under the coil rack, the magnetic ring surrounds the magnetic core, a gap is kept between the magnetic ring and the magnetic core to form a magnetic field, the coil rack is sleeved on the magnetic core and is disposed in the gap.

12 Claims, 2 Drawing Sheets

(51) Int. Cl.
*F16K 31/08* (2006.01)
*A61M 16/20* (2006.01)
*G05D 7/06* (2006.01)

(56) References Cited

U.S. PATENT DOCUMENTS

| | | | |
|---|---|---|---|
| 6,719,268 B2 * | 4/2004 | Fukano et al. | 251/129.17 |
| 6,722,629 B1 * | 4/2004 | Nakazawa | 251/129.17 |
| 6,910,674 B2 * | 6/2005 | Niemela et al. | 251/129.17 |
| 2001/0017360 A1 * | 8/2001 | Watanabe et al. | 251/129.17 |

FOREIGN PATENT DOCUMENTS

| | | |
|---|---|---|
| CN | 201921250 U | 8/2011 |
| DE | 275509 A1 | 1/1990 |
| JP | 2003019201 A | 1/2003 |

* cited by examiner

FLOW CONTROL PROPORTIONAL VALVE

FILED OF THE INVENTION

The present invention relates to a flow control proportional valve for controlling a large flow at a low pressure state, and more particularly to a flow control proportional valve for a ventilator using a low-pressure driving gas source.

BACKGROUND OF THE INVENTION

It is well known that the ventilator is an apparatus that can substitute for, control or change human normal physiological respiration, to increase the pulmonary ventilation volume, improve the respiratory function, decrease breathing power consumption and save the cardiac reserve ability. Such ventilator has become an important instrument for clinically salvaging and treating various respiratory failures as well as providing post-anesthesia and postoperative respiratory support. Ventilators include a pneumatic and electrically controlled ventilator, a pneumatic and pneumatically controlled ventilator, and an electric and electrically controlled ventilator, in terms of their control manners.

Presently, high-pressure gas is generally used by common pneumatic and electrically controlled ventilators as a driving gas source. In flow proportional valves used by most existing pneumatic and electrically controlled ventilators, an actuating element controlled by a voice coil motor is used to compress an elastic element to cause a linear displacement of the elastic element, which alters a throttle area of a fluid passage, thereby controlling the gas flow. However, an opening area of such proportional valve (i.e., a drift diameter) is relatively small, therefore the output pressure of the driving gas source is generally high in order to meet a flow requirement needed by the pneumatic and electrically controlled ventilator, as a result, the applicability of the pneumatic and electrically controlled ventilator is limited to locations, such as a hospital, where the required sufficient high-pressure driving gas source can be offered.

However, with the increasingly extended applicability of ventilators, the traditional pneumatic and electrically controlled ventilator cannot meet some usage requirements for the ventilator in some specific environment due to its excessive usage limitations. For example, when the ventilator is used for salvage in some place, such as outdoors, where a high-pressure driving gas source is insufficient or even unavailable, it is difficult to provide a steady and sufficient high-pressure driving gas source to the ventilator, thus the pneumatic and electrically controlled ventilator cannot provide a satisfying flow and therefore cannot work normally. In this case, the electric and electrically controlled ventilator, which uses only oxygen as a gas source and needs no high-pressure gas source, is usually used to supply gas to a patient under the standard atmosphere.

The electric and electrically controlled ventilator generally adopts a low-pressure gas source provided by a turbine as the driving gas source. However, since the turbine has a low trigger sensitivity and long inspiration response time, the electric and electrically controlled ventilator sometimes cannot be well synchronous with the breathing of a patient. The reason is that, when the low-pressure driving gas source is adopted, a flow proportional valve used by the electric and electrically controlled ventilator has a relatively small drift diameter, and the electric and electrically controlled ventilator can adopt only such a manner that its gas flow is controlled through directly controlling the rotate speed of the turbine. However, since a response speed of the turbine is not fast enough, the service life of the turbine would be affected by frequent acceleration and deceleration for long time of the turbine, thus the application of the electric and electrically controlled ventilator is also restricted.

SUMMARY OF THE INVENTION

An object of the present invention is to provide a flow control proportional valve, which is applicable to a ventilator adopting a low-pressure driving gas source and can ensure a sufficient gas flow needed for the normal operation of the ventilator even when the pressure of the driving gas source is low, and is advantageous for its simple structure, rapid response speed, long service life, etc.

The above object of the present invention can be realized by the following technical solution.

A flow control proportional valve includes a valve body and a valve core arranged below the valve body, a valve cover plate is arranged on an upper end of the valve core, the bottom of the valve cover plate is connected with an upper end of a connecting rod, a coil rack fixedly mounted on a lower end of the connecting rod is wound by a enameled wire which is connected with a power supply unit, a magnetic core and a magnet ring are arranged below the coil rack, the magnet ring is arranged around the magnetic core, a gap exists and a magnetic field is formed between the magnetic core and the magnet ring, and the coil rack receives the magnetic core and is located in the gap between the magnetic core and the magnet ring.

Further, the valve body is provided with an internal cavity which is in communication with a gas inlet and a gas outlet arranged on the valve body, the gas inlet includes a valve port within the cavity, and the valve port is opposite to the valve cover plate.

Further, the magnetic core presents an inverted T-shaped structure, and the magnet ring is arranged around a central part of the magnetic core and fixedly mounted on a base part of the magnetic core at its lower side, such that the gap is formed between the magnetic core and the magnet ring.

Further, the central part of the magnetic core is provided with a through hole, the lower end of the connecting rod is extended through the coil rack and placed in the through hole, and the coil rack receives the central part of the magnetic core.

Further, a shaft sleeve is arranged at an end of the through hole of the central part of the magnetic core that receives the connecting rod.

Further, the shaft sleeve is made of material with a low friction coefficient.

Further, an airtightly sealing means, which includes a membrane, a membrane support and a membrane cover plate, is arranged between the valve body and the magnetic core as well as the magnet ring, the membrane support and the membrane cover plate, each of which includes a center hole, are placed to overlap each other, the connecting rod passes through the center holes of the membrane support and the membrane cover plate, is connected with the valve cover plate at its upper end and extended through the coil rack at its lower end, and the membrane has a ring-shaped structure, an outer perimeter of which is fixed between the membrane support and the membrane cover plate, while an inner perimeter of which is fixedly mounted on the connecting rod.

Further, the membrane cover plate is connected with the valve body at its upper side and a sealing unit is arranged at the connecting portion between the membrane cover plate and the valve body, a lower side of the membrane support is fixedly connected with an upper end of a upper magnetic base, a lower end of the upper magnetic base is arranged between the magnetic core and the magnet ring and is fixed on a sleeve inside of the magnet ring, and a lower side of the upper magnetic base is fixed to an upper side of the magnet ring.

Further, the sealing unit is a sealing ring.

Further, a wiring terminal is mounted on the upper end of the upper magnetic base, one end of the wiring terminal is connected with the enameled wire, and the other end of the wiring terminal is connected with the power supply unit.

The present invention is advantageous as follows. In the flow control proportional valve, the coil rack is placed in the magnetic field produced between the magnetic core and the magnet ring, an electromagnetic force generated in the magnetic field when a current flows through the enameled wire on the coil rack drives the connecting rod and the valve cover plate to move in the axial direction, thereby controlling the opening and closing of the valve port, thus the valve has a simple structure and is easy to realize. With the steady pressure and flow of the input gas, the control on the opening degree and the flow of the valve port may be achieved by varying the value of the input voltage applied across the enameled wire, so that the control on a large flow can be achieved when the low-pressure driving gas source is adopted, to enable the ventilator to work normally. The reciprocating motion of the valve cover plate is implemented by electromagnetic induction, resulting in a high repeat precision and a rapid response speed. Since the coil rack receives the magnetic core and the connecting rod is inserted into the through hole in the central part of the magnetic core, the valve cover plate may be guided during its axial reciprocating motion, so that the precision in opening and closing the valve port is improved, thereby enhancing the precision in controlling the flow. Since the shaft sleeve made of material of a low friction coefficient is arranged at an end of the through hole of the central part of the magnetic core that receives the connecting rod, the reciprocating motion of the connecting rod becomes smoother and the response speed may be enhanced; further, the friction force between the connecting rod and the through hole in the central part of the magnetic core is decreased, the service life of the connecting rod may be prolonged, that is, the service life of the entire valve core may be prolonged. The airtightly sealing means including the membrane, the membrane support and the membrane cover plate is arranged between the valve body and the magnetic core as well as the magnet ring, the outer perimeter of the membrane is mounted between the membrane support and the membrane cover plate while the inner perimeter of the membrane is fixedly mounted on the connecting rod, so that the sealing between the valve body and the magnetic core as well as the magnet ring can be achieved even during the reciprocating motion of the connecting rod, so that the gas flow within the valve body may be more precise, meanwhile the valve core is protected, and the safety, reliability and the service life of the valve core is improved. The sealing ring is arranged where the upper side of membrane cover plate is connected with the valve body, to improve the sealability of the valve body, so that the precision of the gas flow within the valve body can be further improved.

BRIEF DESCRIPTION OF THE DRAWINGS

The present invention will be further described in detail below according to the accompanying drawings and embodiments.

Figure 1:
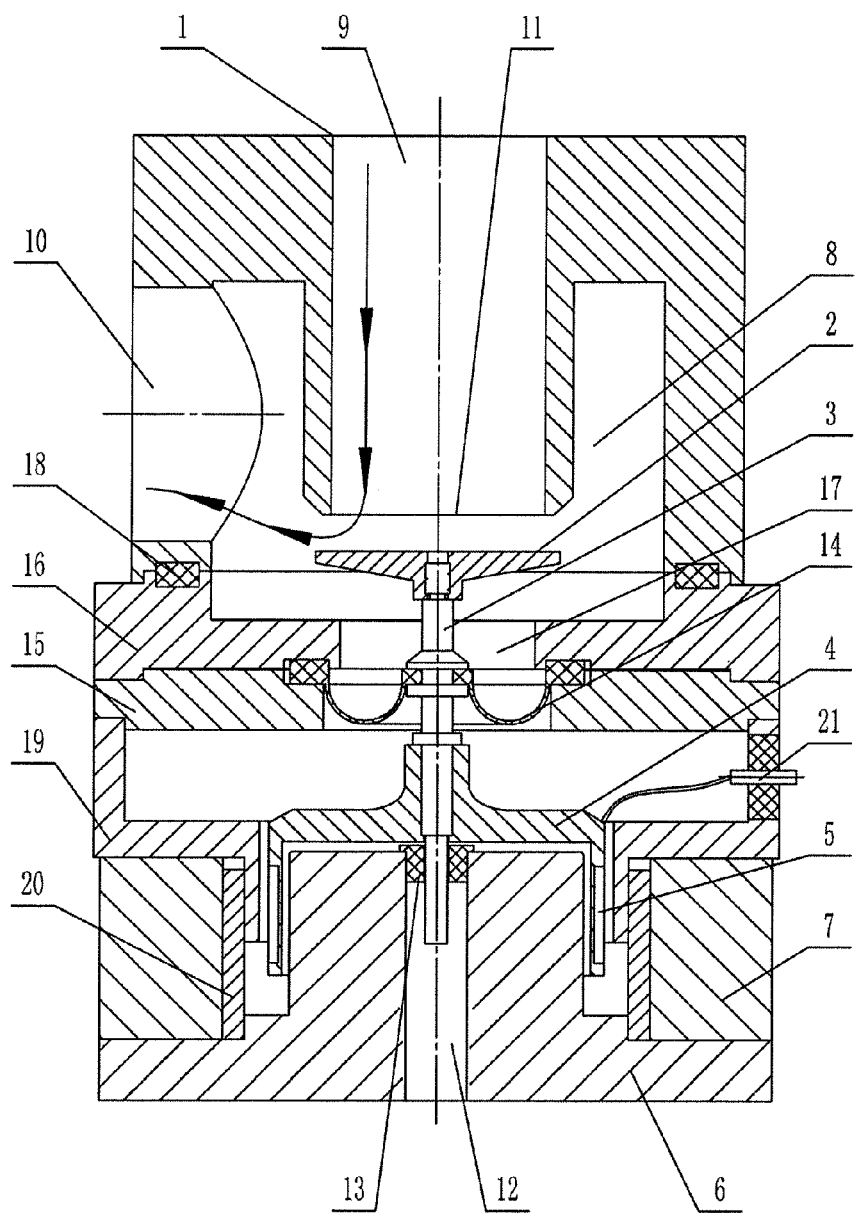
FIG. 1 is a schematic structural diagram of a flow control proportional valve at an open state according to the present invention.

| Reference numeral list: | | | |
|---|---|---|---|
| 1: valve body | 2: valve cover plate | 3: connecting rod | 4: coil rack |
| 5: enameled wire | 6: magnetic core | 7: magnet ring | 8: cavity |
| 9: gas inlet | 10: gas outlet | 11: valve port | 12: through hole |
| 13: shaft sleeve | 14: membrane | 15: membrane support | |
| 16: membrane cover plate | 17: center hole | 18: sealing ring | |
| 19: upper magnetic base | 20: isolating sleeve | 21: wiring terminal | |

DETAILED DESCRIPTION OF THE EMBODIMENTS

Figure 2:
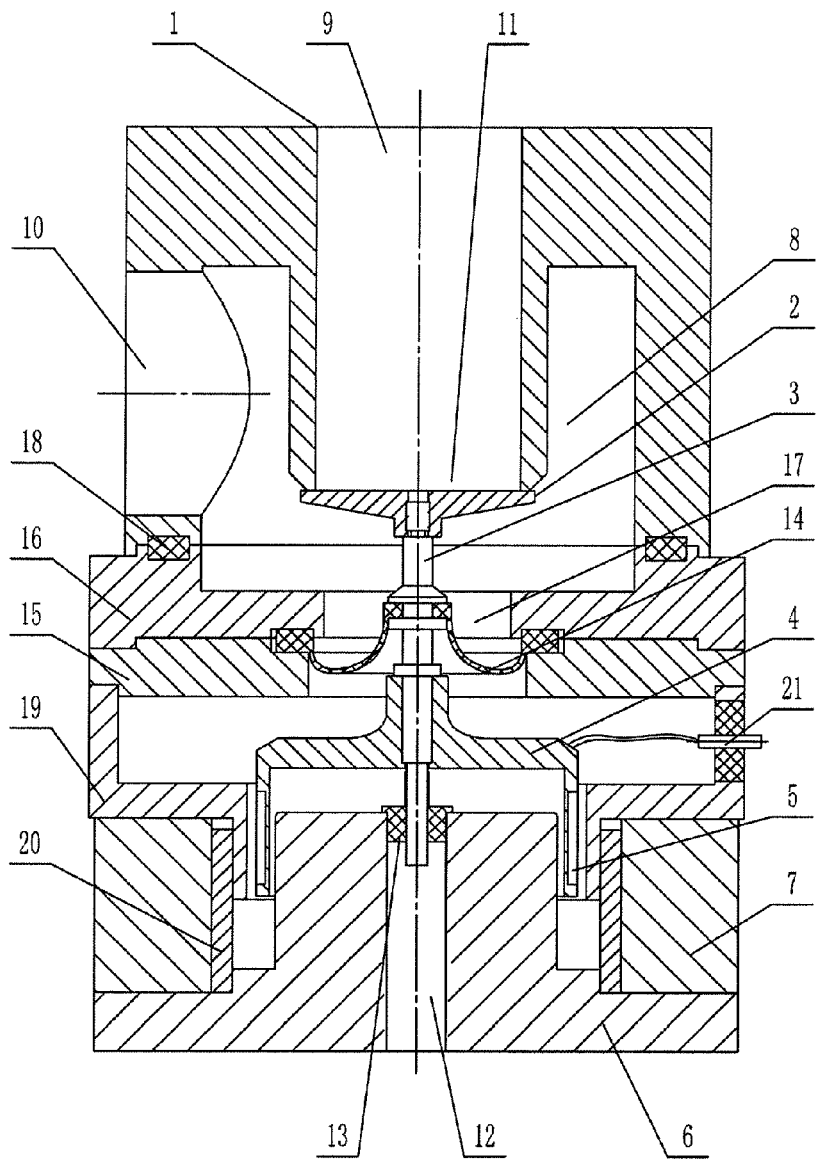
FIG. 2 is a schematic structural diagram of the flow control proportional valve at a closed state according to the present invention.

As shown in FIGS. 1 and 2, a flow control proportional valve in preferred embodiments of the present invention includes a valve body 1 and a valve core, the valve body 1 is provided with an internal cavity 8 which is in communication with a gas inlet 9 and a gas outlet 10 arranged on the valve body 1, and the gas inlet 9 includes a valve port 11 within the cavity 8. A valve core is arranged below the valve body 1, and a valve cover plate 2 is provided on an upper end of the valve core and is placed opposite the valve port 11. The bottom of the valve cover plate 2 is connected with a connecting rod 3, a coil rack 4 fixedly mounted at a lower end of the connecting rod 3 is wound by an enameled wire 5, a magnetic core 6 and a magnet ring 7 are arranged below the coil rack 4, where the magnetic core 6 presents an inverted T-shape structure, and the magnet ring 7 is arranged around the central part of the magnetic core 6 and fixedly mounted on the base part of the magnetic core 6 at its lower side, forming a gap between the magnet ring 7 and the central part of the magnetic core, such that a magnetic field is formed between the magnetic ring 7 and the central part of the magnet core 6. The central part of the magnetic core 6 is provided with a through hole 12, the lower end of the connecting rod 3 is extended through the coil rack 4 and placed in the through hole 12, and a shaft sleeve 13 made of material with a low friction coefficient is arranged at an end of the through hole 12 of the central part of the magnetic core 6 that receives the connecting rod 3, further, the central part of the magnetic core 6 is received in the coil rack 4 so that the enameled wire 5 is placed in the magnetic field formed between the magnetic core 6 and the magnet ring 7. The gas inlet 9 is connected with a turbine-type gas supply unit.

Further, an airtightly sealing means, which includes a membrane 14, a membrane support 15 and a membrane cover plate 16, is arranged between the valve body 1 and the magnetic core 6 as well as the magnet ring 7. The membrane support 15 and the membrane cover plate 16, each of which includes a center hole 17 at the center, are placed to overlap each other, and the connecting rod 3 passes through the center holes 17 of the membrane support 15 and the membrane cover plate 16, is connected with the valve cover plate 2 at its upper end and extended through the coil rack 4 at its lower end. The membrane 14 has a ring-shaped structure, an outer perimeter of which is fixed between the membrane support 15 and the membrane cover plate 16, while an inner perimeter of which is fixedly mounted on the connecting rod 3. The membrane cover plate 16 is connected with the valve body 1 at its upper side and a sealing ring 18 is arranged at the connecting portion between the membrane cover plate 16 and the valve body 1. A lower side of the membrane support 15 is fixedly connected with an upper end of an upper magnetic base 19, a lower end of the upper magnetic base 19 is inserted in the gap between the magnetic core 6 and the magnet ring 7 and is fixed on a sleeve 20 inside of the magnet ring 7, and a lower side of the upper magnetic base 19 is fixed to an upper side of the magnet ring 7. A wiring terminal 21 is mounted on the upper end of the upper magnetic base 19, one end of the wiring terminal 21 is connected with the enameled wire 5 wound on the coil rack 4, and the other end of the wiring terminal 21 is connected with a power supply unit.

Operation of the Flow Control Proportional Valve

As shown in FIG. 1, when the power supply unit is powered on to apply a voltage to the enameled wire 5 by the wiring terminal 21, current flows through the enameled wire 5, which is hence under the action of an electromagnetic force in the magnetic field formed between the magnetic core 6 and the magnet ring 7. In this case, the coil rack 4 is pushed by the electromagnetic force, thus driving the connecting rod 3 and the valve cover plate 2 to move in an axial direction along the through hole 12 in the central part of the magnetic core 6, while the shaft sleeve 13 plays a role of guiding the connecting rod 3. Depending on a different pulse voltage applied to the enameled wire 5, the coil rack 4 together with the connecting road 3 and the valve cover plate 2 are moved to a different position under the action of the electromagnetic force. When the voltage is small, the electromagnetic force is smaller than the pressure of the flow at the gas inlet 9 that is applied to the valve cover plate 2. At this time, a low-pressure driving gas source supplied by the turbine-type gas supply unit flows into the cavity 8 through the gas inlet 9 and the valve port 11, and flows out from the gas outlet 10 through the gap between the valve port 11 and the valve cover plate 2, to achieve the gas supply by the low-pressure gas source. The membrane 14 is used for sealing, to isolate the cavity 8 within the valve body 1 from a cavity formed by the magnetic core 6 and the magnet ring 7, such that the gas cannot flow into the cavity formed by the magnetic core 6 and the magnet ring 7, thereby protecting the electromagnetic driving unit. In the situation, the flow outputted from the valve body may be varied with the voltage input to the flow control proportional valve.

As shown in FIG. 2, because the pressure and flow of the low-pressure driving gas source supplied by the turbine-type gas supply unit is stable, an increase of the voltage applied on the enameled wire 5 causes an increase of the electromagnetic force applied on the coil rack 4 and the connecting rod 3 as well as the valve cover plate 2. When such electromagnetic force is more than the pressure and gas resistance on the valve cover plate 2 applied by the gas at the valve port 11, the valve cover plate 2 is moved upwards and closes the valve port 11, thus the low-pressure driving gas source supplied by the turbine-type gas supply unit cannot flow from the gas inlet 9 to the gas outlet 10, thereby closing the flow control proportional valve.

The flow control proportional valve is described above to be used for the ventilator using the low-pressure driving gas source, but not limited thereto. For the person skilled in the art, any other flow control proportional valves having a structure similar to the above structure should fall into the scope of the invention.

The flow control proportional valve, which is applicable to a ventilator adopting a low-pressure driving gas source, can ensure a sufficient gas flow needed for the normal operation of the ventilator even when the pressure of the driving gas source is low, and is advantageous for its simple structure, rapid response speed, long service life, etc.

What is claimed is:

1. A flow control proportional valve, comprising a valve body and a valve core, characterized in that, the valve core is arranged below the valve body, a valve cover plate is arranged on an upper end of the valve core, the bottom of the valve cover plate is connected with an upper end of a connecting rod, a coil rack fixedly mounted on a lower end of the connecting rod is wound by a enameled wire which is connected with a power supply unit, a magnetic core and a magnet ring are arranged below the coil rack, the magnet ring is arranged around the magnetic core, a gap exists and a magnetic field is formed between the magnetic core and the magnet ring, and the coil rack receives the magnetic core and is located in the gap between the magnetic core and the magnet ring;

wherein, an air tight sealing means, which includes a membrane, a membrane support and a membrane cover plate, is arranged between the valve body and the magnetic core as well as the magnet ring, the membrane support and the membrane cover plate, each of which includes a center hole, are placed to overlap each other, the connecting rod passes through the center holes of the membrane support and the membrane cover plate, is connected with the valve cover plate at its upper end and extended through the coil rack at its lower end, and the membrane has a ring-shaped structure, an outer perimeter of which is fixed between the membrane support and the membrane cover plate, while an inner perimeter of which is fixedly mounted on the connecting rod.

2. The flow control proportional valve of claim 1, wherein, the valve body is provided with an internal cavity, which is in communication with a gas inlet and a gas outlet arranged on the valve body, the gas inlet includes a valve port within the cavity, and the valve port is opposite to the valve cover plate.

3. The flow control proportional valve of claim 1, wherein, the magnetic core presents an inverted T-shaped structure, and the magnet ring is arranged around a central part of the magnetic core and fixedly mounted on a base part of the magnetic core at its lower side, such that the gap is formed between the magnetic core and the magnet ring.

4. The flow control proportional valve of claim 1, wherein, the central part of the magnetic core is provided with a through hole, the lower end of the connecting rod is extended through the coil rack and placed in the through hole, and the coil rack receives the central part of the magnetic core.

5. The flow control proportional valve of claim 4, wherein, a shaft sleeve is arranged at an end of the through hole of the central part of the magnetic core that receives the connecting rod.

6. The flow control proportional valve of claim 5, wherein, the shaft sleeve is made of material with a low friction coefficient.

7. The flow control proportional valve of claim 1, wherein, the membrane cover plate is connected with the valve body at its upper side and a sealing unit is arranged at the connecting portion between the membrane cover plate and the valve body, a lower side of the membrane support is fixedly connected with an upper end of an upper magnetic base, a lower end of the upper magnetic base is arranged between the magnetic core and the magnet ring and is fixed on a sleeve inside of the magnet ring, and a lower side of the upper magnetic base is fixed to an upper side of the magnet ring.

8. The flow control proportional valve of claim 7, wherein, the sealing unit is a sealing ring.

9. The flow control proportional valve of claim 7, wherein, a wiring terminal is mounted on the upper end of the upper magnetic base, one end of the wiring terminal is connected with the enameled wire, and the other end of the wiring terminal is connected with the power supply unit.

10. The flow control proportional valve of claim 3, wherein, the central part of the magnetic core is provided with a through hole, the lower end of the connecting rod is extended through the coil rack and placed in the through hole, and the coil rack receives the central part of the magnetic core.

11. The flow control proportional valve of claim 10, wherein, a shaft sleeve is arranged at an end of the through hole of the central part of the magnetic core that receives the connecting rod.

12. The flow control proportional valve of claim 11, wherein, the shaft sleeve is made of material with a low friction coefficient.

* * * * *